United States Patent [19]

Rebrovic et al.

[11] Patent Number: 6,153,783

[45] Date of Patent: Nov. 28, 2000

[54] METHOD FOR PREPARING A DIFUNCTIONAL ALIPHATIC ORGANIC COMPOUND

[75] Inventors: Louis Rebrovic, Ross; Michael Staley, Cincinnati, both of Ohio

[73] Assignee: Cognis Corporation, Gulph Mills, Pa.

[21] Appl. No.: 09/478,555

[22] Filed: Jan. 6, 2000

[51] Int. Cl.[7] .......................... C07C 255/00; C07C 69/00; C07C 67/00; C07C 57/02; C07C 233/00
[52] U.S. Cl. .......................... 558/440; 560/129; 560/204; 562/598; 564/123
[58] Field of Search .............................. 558/440; 560/129, 560/204; 562/598; 564/123

[56] References Cited

U.S. PATENT DOCUMENTS

| | | |
|---|---|---|
| 4,322,547 | 3/1982 | Minisci et al. . |
| 5,380,928 | 1/1995 | Malek et al. . |
| 5,872,267 | 2/1999 | Cotarca et al. . |

FOREIGN PATENT DOCUMENTS

WO 94/29257   12/1994   WIPO .

OTHER PUBLICATIONS

Cotarca et al., "Efficient Synthesis of ω–Functionalized Nonanoic Acids" (1996) pp. 328–332.

*Primary Examiner*—Joseph K. McKane
*Assistant Examiner*—Joseph Murray
*Attorney, Agent, or Firm*—John E. Drach; Michael E. Carmen

[57] ABSTRACT

A two-step process for producing a difunctional organic compound is provided which comprises:

a) reacting a cycloalkanone with a 2-substituted-1-alkene in the presence of an enamine catalyst to produce the corresponding substituted cycloalkanone intermediate and, b) subjecting the intermediate reaction product to ultraviolet radiation in the presence of a solvent to form the difunctional organic compound of the general formula:

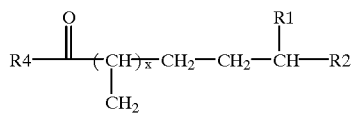

wherein R4 is derived from the solvent and is hydroxyl, $-NH_2$ or $OR^5$, and wherein R, R1, R2, R4, $R^5$, and x are as defined in the specification.

23 Claims, No Drawings

METHOD FOR PREPARING A DIFUNCTIONAL ALIPHATIC ORGANIC COMPOUND

BACKGROUND OF THE INVENTION

1. Field of the Invention

This invention relates to a method for preparing a difunctional aliphatic organic compound. More particularly, the difunctional aliphatic organic compound described herein, e.g., a dicarboxylic acid, diester or a derivative thereof, is produced by a two-step method employing ultraviolet radiation.

2. Brief Description of the Prior Art

In general, methods for producing difunctional aliphatic organic compounds are known. For example, U.S. Pat. No. 4,322,547 discloses a method for preparing a difunctional aliphatic organic compound. The method involves (1) reacting hydrogen peroxide with a cyanoethyl derivative of cycloaliphatic ketone to obtain a hydroperoxide; (2) catalytically splitting the hydroperoxide in an aqueous or aqueous-organic medium by adding a catalyst consisting of ferrous salts and cupric salts to obtain an unsaturated difunctional acid; and (3) catalytically hydrogenating the unsaturated acid in an organic solvent in the presence of a catalyst to obtain the product saturated difunctional aliphatic organic compound. This method is limited to where the cycloaliphatic ketone is cyclopentanone or cyclohexanone.

Another example is U.S. Pat, No. 5,872,267 which discloses a five-step method for making azelaic acid, i.e., a dicarboxylic acid. The method involves (1) adding cyclohexanone to a propionitrile to form 3-(2-cyclohexanonyl) propionitrile; (2) oxidizing the propionitrile to the corresponding lactone, 7-cyanoethyl-2-oxepanone; (3) pyrolyzing the lactone at 450° C.; (4) hydrogenating the pyrolyzed lactone; and (5) hydrolyzing the hydrogenated product to provide the product azelaic acid.

It would be desirable to provide a method for producing a difunctional aliphatic organic compound such as a dicarboxylic acid, e.g., azelaic acid, diester or a derivative thereof which requires a minimum number of steps.

SUMMARY OF THE INVENTION

In accordance with the present invention, a novel two-step method of preparing a difunctional aliphatic organic compound is provided which comprises:

a) reacting a cycloalkanone of the general formula

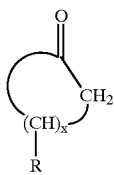

wherein x is an integer from 2 to 9; each R is the same or different and is hydrogen, a linear or branched alkyl, alkylaryl, hydroxyl or a halogen with a compound of the general formula

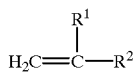

wherein $R^1$ is hydrogen or alkyl; $R^2$ is —COOH or a salt thereof, —CN, —CONH$_2$ or —COOR$^3$ wherein $R^3$ is a linear or branched alkyl or aryl, in the presence of a catalyst to provide an intermediate reaction product of the general formula

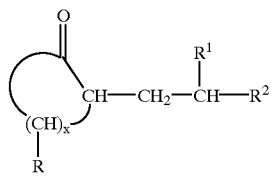

wherein x, R, $R^1$, $R^2$ and $R^3$ have the aforestated meanings; and, b) subjecting the intermediate reaction product to ultraviolet radiation in the presence of a solvent to produce the product difunctional aliphatic organic compound of the general formula

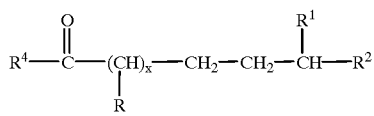

wherein $R^4$ is derived from the solvent and is hydroxyl, —NH$_2$ or OR$^5$ wherein $R^5$ is an alkyl or aryl, and x, R, $R^1$, and $R^2$ have the aforestated meanings.

In one embodiment of the present invention, a dicarboxylic acid is provided which comprises:

a) reacting a cycloalkanone of the general formula

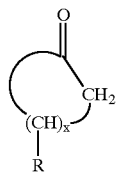

wherein x is an integer from 2 to 9; each R is the same or different and is hydrogen, a linear or branched alkyl, alkylaryl, hydroxyl or a halogen with a compound of the general formula

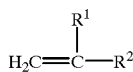

wherein $R^1$ is hydrogen or alkyl and $R^2$ is —COOH, or —CN in the presence of a catalyst to obtain an intermediate reaction product of the general formula

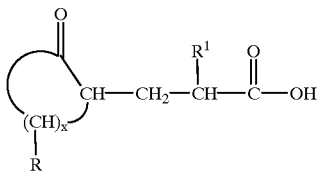

wherein x, R, $R^1$ and $R^2$ have the aforestated meanings; and, b) subjecting the intermediate reaction product to ultraviolet light in the presence of water to provide the product dicarboxylic acid of the general formula

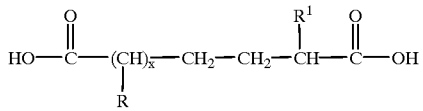

wherein x, R and $R^1$ have the aforestated meanings.

In a second embodiment of the present invention, a diester is provided which comprises:

a) reacting a cycloalkanone of the general formula

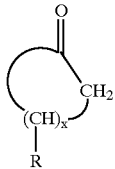

wherein x is an integer from 2 to 9; each R is the same or different and is hydrogen, a linear or branched alkyl, alkylaryl, hydroxyl or a halogen with a compound of the general formula

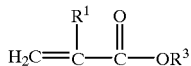

wherein $R^1$ is hydrogen or alkyl and $R^3$ is a linear or branched alkyl or aryl in the presence of a catalyst to provide an intermediate reaction product of the general formula

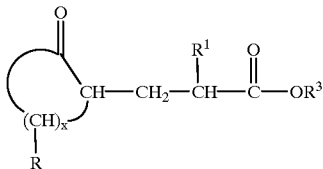

wherein x, R, $R^1$ and $R^3$ have the aforestated meanings; and, b) subjecting the intermediate reaction product to ultraviolet light in the presence of an alcohol of the general formula $R^5$—OH wherein $R^5$ is an alkyl or aryl to provide the product diester of the general formula

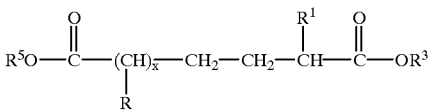

wherein x, R, $R^1$, $R^3$ and $R^5$ have the aforestated meanings.

In yet another embodiment of the present invention, a dicarboxylic acid monoester is provided which comprises:

a) reacting a cycloalkanone of the general formula

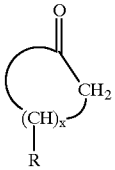

wherein x is an integer from 2 to 9; each R is the same or different and is hydrogen, a linear or branched alkyl, alkylaryl, hydroxyl or a halogen with a compound of the general formula

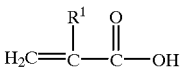

wherein $R^1$ is hydrogen or alkyl in the presence of a catalyst to provide an intermediate reaction product of the general formula

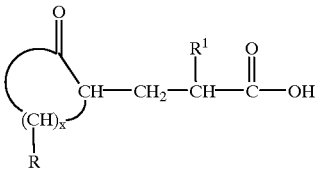

wherein x, R and $R^1$ have the aforestated meanings; and, b) subjecting the intermediate reaction product to ultraviolet radiation in the presence of an alcohol of the general formula $R^5$—OH wherein $R^5$ is an alkyl or aryl to provide the product dicarboxylic acid monoester of the general formula

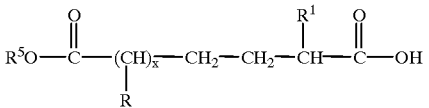

wherein x, R, $R^1$ and $R^5$ have the aforestated meanings.

It is also contemplated that the foregoing dicarboxylic acid monoester can be obtained from the method described herein when $R^2$ is —$COOR^3$ and the solvent employed in step (b) is water.

In yet another embodiment of the present invention, a dicarboxylic monoamide is provided which comprises:

a) reacting a cycloalkanone of the general formula

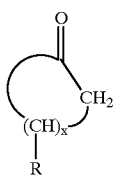

wherein x is an integer from 2 to 9; each R is the same or different and is hydrogen, a linear or branched alkyl, alkylaryl, hydroxyl or a halogen with a compound of the general formula

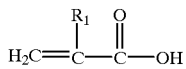

wherein $R^1$ is hydrogen or alkyl in the presence of a catalyst to provide an intermediate reaction product of the general formula

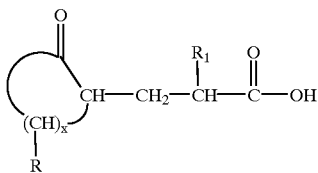

wherein x, R and $R^1$ have the aforestated meanings; and, b) subjecting the intermediate reaction product to ultraviolet radiation in the presence of an amine to provide the product dicarboxylic acid monoamide of the general formula

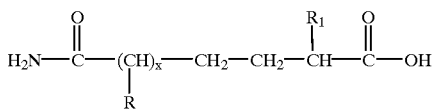

wherein x, R and $R^1$ have the aforestated meanings.

It is also contemplated that the foregoing dicarboxylic acid monoamide can be obtained from the method described herein when $R^2$ is —$CONH_2$ and the solvent employed in step (b) is water.

Unlike the other known methods previously described to produce a difunctional aliphatic organic compound, the method described herein advantageously produces a difunctional aliphatic organic compound such as a dicarboxylic acid, a diester or derivatives thereof by a two-step process that employs ultraviolet radiation. Additionally, the by-products formed from this method can be readily converted to the intermediate reaction product and/or resulting product difunctional aliphatic organic compound. Accordingly, the method described herein can provide a substantially higher purity product in a more economically feasible time.

DESCRIPTION OF THE PREFERRED EMBODIMENTS OF THE INVENTION

The difunctional aliphatic organic compound of this invention possesses the general formula

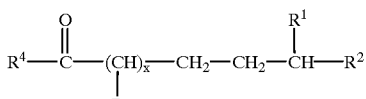

wherein x is an integer from about 2 to about 9 and preferably from about 5 to about 7; each R is the same or different and is hydrogen, a straight or branched alkyl group of from about 1 to about 25 carbon atoms, a hydroxyl, a halogen, e.g., bromine, chlorine, fluorine, etc., or an alkylaryl where the alkyl group is from 4 to about 30 carbon atoms, including, by way of illustration, unsubstituted straight or branched aliphatic, cycloaliphatic and aromatic groups and cycloaliphatic and aromatic groups substituted with one or more straight or branched aliphatic, cycloaliphatic and/or aromatic groups; $R^1$ is hydrogen or an alkyl group of from about 1 to about 25 carbon atoms; $R^2$ is —COOH or a salt thereof, e.g., sodium, potassium, etc., —CN, —$CONH_2$ or —$COOR^3$ wherein $R^3$ is a linear or branched alkyl of from about 1 to about 25 carbon atoms and preferably from about 1 to about 3 carbon atoms or an aryl, and $R^4$ is hydroxyl, —$NH_2$ or —$OR^5$ wherein $R^5$ is an alkyl of from about 1 to about 25 carbon atoms and preferably from about 1 to about 3 carbon atoms or an aryl.

The foregoing difunctional aliphatic organic compound of this invention can be obtained by first reacting a substituted or unsubstituted cycloalkanone of the general formula

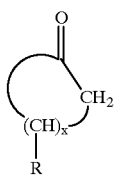

wherein x and R have the aforestated meanings with a compound of the general formula $R^1$

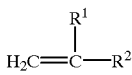

wherein $R^1$ and $R^2$ have the aforestated meanings in the presence of a catalyst to form the intermediate reaction product of the general formula

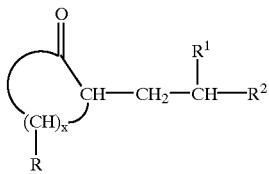

wherein x, R, $R^1$ and $R^2$ have the aforestated meanings.

Suitable unsubstituted cycloalkanones for use herein include cyclobutanone, cyclopentanone, cyclohexanone, cycloheptanone, cyclooctanone, cyclononanone, cyclodecanone and cycloundecanone with cyclohexanone being preferred. If desired, the cycloalkanone can be substituted with at least one substituent thereon, i.e., substituent R as defined above.

The compound to react with the cycloalkanone will vary according to the desired intermediate reaction product, e.g., a carboxylic acid, an ester, etc., and subsequent difunctional aliphatic organic compound product, e.g., a carboxylic acid, a dicarboxylic acid, an ester, a diester, etc., which is described hereinbelow. Thus, as one skilled in the art will readily appreciate, when forming a carboxylic acid as the intermediate reaction product, $R^2$ can be —COOH. Additionally, when forming an ester as the intermediate reaction product, $R^2$ can be —COOR$^3$. It is also contemplated that the compound can possess a substituent thereon, i.e., substituent $R^1$ described above.

The reaction of the cycloalkanone and the compound can be carried out according to methods known to one skilled in the art, e.g., such as those described in U.S. Pat. No. 5,872,267, the contents of which are incorporated by reference herein. In general, the cycloalkanone is advantageously reacted with the compound to form the intermediate reaction product in a mole ratio ranging from about 4 to about 1, preferably from about 1.5 to about 1 and more preferably from about 1 to about 1. The reaction is ordinarily conducted at a temperature ranging from about 100° C. to about 170° C. and preferably from about 130° C. to about 165° C. The time for the reaction to be completed will generally range from about 30 minutes to about 4 hours.

The reaction between the cycloalkanone and the foregoing compound can take place in the presence of a catalyst. Suitable catalysts for use herein include carboxylic acids, amines, mixtures thereof and the like. Useful amines include enamines and the like. Useful enamines include, but are not limited to, 1-pyrrolidino-1-cyclohexene, 1-morpholino-1-cylohexene, 1-pyrrolidino-1-cyclopentene and the like, with 1-pyrrolidino-1-cyclohexene being preferred for use herein. When employing the catalyst in the method described herein, small amounts of water can be added to the reaction if desired. In general, in the case where water is added to the reaction and the catalyst is enamine, the amount of enamine can range from a concentration of from about 0.5 to about 5 percent and preferably from about 2 to about 4 percent and the amount of water can range from a concentration of from about 0.05 to about 1 percent and preferably from about 0.1 to about 0.4 percent.

Once the intermediate reaction product is formed, it is then cooled at room temperature and can be further separated from any residual cycloalkanone and/or the compound and any minor by-products by employing conventional methods known to those skilled in the art, e.g., by fractional distillation and/or solvent crystallization.

A major by-product that can be produced during formation of the intermediate reaction product and/or during the separation of any of the remaining residual and/or minor by-product is, for example, a corresponding enol lactone, which can be readily hydrolyzed back to the intermediate reaction product by adding water to the enol lactone and heating the mixture.

Next, the purified intermediate reaction product is subjected to ultraviolet radiation in the presence of a solvent to provide the product difunctional aliphatic organic compound of this invention. Any conventional source of ultraviolet radiation known to one skilled in the art can be used herein, e.g., a mercury lamp, high intensity lamp, etc. Typically, the ultraviolet radiation will be applied at an electrical power ranging from about 200 to about 600 watts, preferably from about 300 to about 500 watts and more preferably from about 400 to about 450 watts, for a time period ranging from about 0.5 to about 48 hours and preferably from about 2 to about 24 hours. This reaction is ordinarily carried out at room temperature in the presence of an inert gas. Suitable inert gases for use herein include, for example, nitrogen, argon, carbon dioxide and the like with nitrogen being preferred.

Suitable solvents for use herein include alcohol and water, both of which can be used in combination with a carboxylic acid solvent. As one skilled in the art will readily appreciate, the type of solvent employed will determine the desired difunctional aliphatic organic compound. Thus, for example, if the desired aliphatic organic compound is a diester, i.e., in the case where $R^2$ is —COOR$^3$, or a derivative thereof, i.e., in the case where $R^2$ is other than COOR$^3$, the solvent used herein is an alcohol of the general formula $$R^5\text{—OH}$$

wherein $R^5$ is an alkyl of from about 1 to about 25 carbon atoms or an aryl. Accordingly, useful alcohols include methanol, ethanol, propanol, butanol, pentanol, hexanol, heptanol, octanol, nonanol, decanol, undecanol, dodecanol, tridecanol, tetradecanol, pentadecanol, phenol and the like with methanol being preferred. Suitable carboxylic acid solvents for use with alcohol are typically low alkyl carboxylic acids of up to about six carbon atoms, e.g., acetic acid, propionic acid, etc.

Additionally, if, for example, the desired aliphatic organic compound is a dicarboxylic acid, i.e., in the case where $R^2$ is —COOH, or a derivative thereof, i.e., in the case where $R^2$ is other than —COOH, the solvent used herein can be water or water in combination with a carboxylic acid solvent as described above.

Further, if, for example, the desired aliphatic organic compound is a half carboxylic acid/amide, i.e., in the case where $R^4$ is $NH_2$, the solvent used herein can be an amine, e.g., octylamine. The amount of solvent employed will ordinarily range from about 40 to about 98 weight percent, preferably from about 50 to about 96 weight percent and more preferably from about 90 to about 95 weight percent, based on the weight of the intermediate reaction product.

In addition to the product difunctional aliphatic organic compound, a by-product can be formed of the general formula

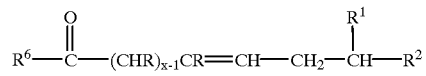

wherein x, R, $R^1$ and $R^2$ have the aforesaid meanings and $R^6$ is a hydrogen, alkyl or aryl.

The by-product can be readily oxidized and hydrogenated by methods well known to those skilled in the art to yield the corresponding diacid, hemiester or diester compound as represented by the difunctional aliphatic organic compound shown above. For example, ultraviolet radiation of the intermediate reaction product 3-(2-oxocyclohexyl) propanoic acid can also result in the formation of the by-product 9-oxononenoic acid which can be oxidized and hydrogenated to yield nonanedioic acid.

The final yield of the difunctional aliphatic organic compound is from about 5 to about 30 weight percent based on the weight of the reaction product. The following examples are illustrative of the method of this the invention.

EXAMPLE 1

This example illustrates the preparation of the compound

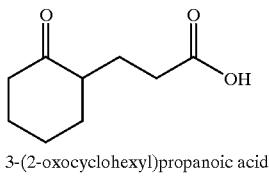

3-(2-oxocyclohexyl)propanoic acid 29.4 Grams (0.300 mol; 31.1 mL) cyclohexanone, 14.4 grams (0.200 mol; 13.7 mL) of acrylic acid, 1.6 mL (9.6× $10^{-3}$ mol) of 1-pyrrolidino-1-cyclohexene and 0.09 grams (5×$10^{-3}$ mol) of water were added to a 250 mL round bottomed flask equipped with a reflux condenser, thermometer, and magnetic stirrer. The mixture was stirred and heated under reflux for four hours. The mixture was then cooled to room temperature resulting in a slushy mixture. Next, the reaction product was subjected to fractional distillation using a 1×20 cm Vigreux column and 0.3 mm Hg vacuum. The fraction taken at 145–151° C. yielded 20.4 g of 91 percent 3-(2-oxocyclohexyl)-propanoic acid (54 percent yield). This fraction was recrystallized in 40 mL CHCl₃/200 mL petroleum ether to give 15.4 grams of 3-(2-oxocyclohexyl)propanoic acid at 99 percent purity.

EXAMPLE 2

This examples illustrates the preparation of the following dicarboxylic acid compound

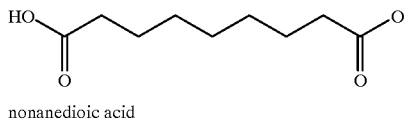

nonanedioic acid

A solution of 20.0 grams (96.4 percent pure; 0.113 mole) of the 3-(2-oxo-cyclohexyl)propanoic acid prepared as described in Example 1 in 300 mL of H₂O and 3.0 grams of (0.075 mole) sodium hydroxide was stirred under a blanket of nitrogen gas and subjected to a 450-Watt medium pressure mercury lamp at ~25° C. for a total of twenty six hours. The mixture was then washed with 3×50 mL of chloroform and subsequently acidified to a pH of 3 with concentrated hydrochloric acid. The volume of the reaction mixture was reduced under rotoevaporation (2 mm of pressure at 95–100° C.) to give 1.22 grams of white crystals composed of 93.5 percent nonanedioic acid. The reaction mixture was further acidified to a pH of 2 with concentrated hydrochloric acid and slowly cooled to 3° C. to provide another crop of white crystals which were then filtered off to give 1.34 grams of 97.2 percent nonanedioic acid. This mixture was subjected to rotoevaporation resulting in a white slush. This slush was washed with methanol and the methanol wash poured into a crystallization dish. The methanol slowly evaporated in the dish and resulted in 5.86 grams of material composed of 34 percent nonanedioic acid.

The total isolated yield of nonanedioic acid was determined to be 21 percent as follows:

$$1.22 \text{ g} \times 0.935 = 1.14 \text{ g}$$
$$1.34 \text{ g} \times 0.972 = 1.30 \text{ g}$$
$$5.86 \text{ g} \times 0.34 = \underline{1.99 \text{ g}}$$
$$4.43 \text{ g}$$

$$\frac{4.43 \text{ g}}{188.22 \text{ g/mole}} \times \frac{1}{0.113 \text{ mole}} \times 100 = 20.8 \text{ percent}$$

The percent of the nonanedioic acid in each crop was determined by an area percent gas liquid chromatography (GLC). The sample was prepared for GLC analysis as follows:

0.10 Grams of the sample was heated under reflux ~4.0 mL of 1 M HCl methanol for 45 minutes. The solution was then cooled to room temperature and neutralized with NaHCO₃. A 0.10 mL sample of this was taken and diluted to 1.0 mL with methanol and injected into the GLC.

EXAMPLE 3

Conversion of the Esters of 3-(2-oxocyclohexyl) propanoic acid to azelate ester

Esters of 3-(2-oxocyclohexyl)propanoic acid can be converted to azelate ester via ultraviolet irradiation in an alcoholic solvent. For example, a 12.5 weight percent methanol solution of methyl 3-(2-oxocyclohexyl)propanoate was irradiated with a 450-Watt medium pressure mercury lamp at 15° C. The results (area percent GLC) were obtained as follows:

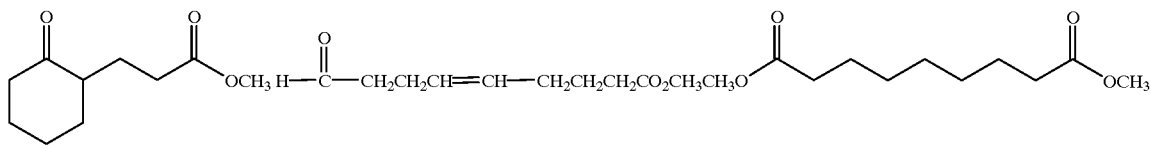

| Time | | | |
|---|---|---|---|
| 1.0 hr. | 83.7 percent | 8.97 percent | 3.87 percent |
| 2.5 hr. | 64.66 percent | 19.48 percent | 9.17 percent |
| 4.0 hr. | 49.95 percent | 27.68 percent | 13.55 percent |

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method for preparing a difunctional aliphatic organic compound which comprises:

a) reacting a cycloalkanone of the general formula

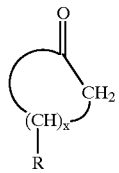

wherein x is an integer from about 2 to 9; each R is the same or different and is hydrogen, a linear or branched alkyl, an alkylaryl, a hydroxyl or a halogen, with a compound of the general formula

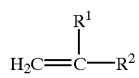

wherein $R^1$ is hydrogen or alkyl; $R^2$ is —COOH or a salt thereof, —CN, —CONH$_2$ or COOR$^3$ wherein $R^3$ is a linear or branched alkyl or aryl in the presence of a catalyst to form an intermediate reaction product of the general formula

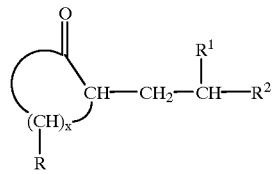

wherein x, R, $R^1$ and $R^2$ have the aforestated meanings; and, b) subjecting the intermediate reaction product to ultraviolet radiation in the presence of a solvent to provide the product difunctional aliphatic organic compound of the general formula

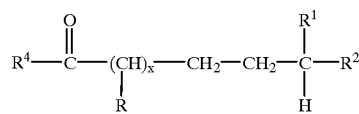

wherein $R^4$ is derived from the solvent and is hydroxyl, —NH$_2$ or —OR$^5$ wherein $R^5$ is an alkyl or aryl, and x, R, $R^1$, and $R^2$ have the aforestated meanings.

2. The method according to claim 1 wherein the catalyst is an enamine.

3. The method according to claim 2 wherein the enamine is selected from the group consisting of 1-pyrrolidino-1-cyclohexene, 1-morpholino-1-cyclohexene, and 1-pyrrolidino-1-cyclopentene.

4. The method according to claim 1 wherein the solvent is alcohol or water.

5. The method according to claim 4 wherein the alcohol is selected from the group consisting of methanol, ethanol, propanol, butanol, pentanol, hexanol, heptanol, octanol, nonanol, decanol, undecanol, dodecanol, tridecanol, tetradecanol, pentadecanol, phenol and mixtures thereof.

6. The method according to claim 4 wherein the alcohol or water is combined with a carboxylic acid.

7. The method according to claim 6 wherein the carboxylic acid is a low alkyl carboxylic acid of up to about six carbon atoms.

8. The method according to claim 1 wherein R is hydrogen, $R^1$ is hydrogen, $R^2$ is —COOH and $R^4$ is hydroxyl.

9. The method according to claim 8 wherein the solvent is water.

10. The method according to claim 1 wherein R is hydrogen, $R^1$ is hydrogen, $R^2$ is COOR$^3$ and $R^4$ is OR$^5$.

11. The method according to claim 10 wherein the solvent is an alcohol.

12. The method according to claim 1 wherein R is hydrogen, $R^1$ is hydrogen, $R^2$ is —COOR$^3$ and $R^4$ is hydroxyl.

13. The method according to claim 12 wherein the solvent is water.

14. The method according to claim 1 wherein R is hydrogen, $R^1$ is hydrogen, $R^2$ is —COOH and $R^4$ is OR$^5$.

15. The method according to claim 14 wherein the solvent is an alcohol.

16. The method according to claim 1 wherein the ultraviolet radiation is applied at a power of from about 200 to about 600 watts.

17. The method according to claim 1 wherein the ultraviolet radiation is applied at a power of from about 300 to about 500 watts.

18. The method according to claim 1 wherein the ultraviolet radiation is applied at a power of from about 400 to about 450 watts.

19. The method according to claim 1 wherein the ultraviolet radiation is applied for a period ranging from about 1 to about 48 hours.

20. A method for preparing a difunctional aliphatic organic compound which comprises:

a) reacting a cycloalkanone of the general formula

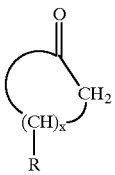

wherein x is an integer from about 3 to 6 and each R is the same or different and is hydrogen, a linear or branched alkyl, an alkylaryl, a hydroxyl or a halogen with a compound of the general formula

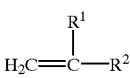

wherein $R^1$ is hydrogen or alkyl, $R^2$ is —COOH or a salt thereof, or COOR$^3$ wherein $R^3$ is a linear or branched alkyl or aryl in the presence of an enamine and water to form an intermediate reaction product of the general formula

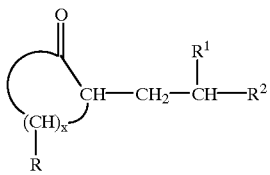

wherein x, R, $R^1$ and $R^2$ have the aforestated meanings; and, b) subjecting the intermediate reaction product to ultraviolet radiation in the presence of a solvent to produce the difunctional aliphatic organic compound of the general formula

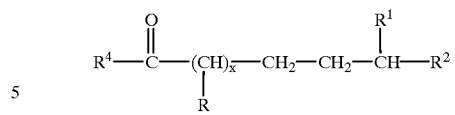

wherein $R^4$ is derived from the solvent and is hydroxyl or —$OR^5$ wherein $R^1$ is an alkyl, and x, $R^1$ and $R^2$ have the aforestated meanings.

21. The method according to claim 20 wherein the solvent is alcohol or water.

22. The method according to claim 20 wherein x is 4, R is hydrogen, $R^1$ is hydrogen, $R^2$ is —COOH, and $R^4$ is hydroxyl.

23. The method according to claim 22 wherein the solvent is water.

* * * * *